(12) United States Patent
Hofmann et al.

(10) Patent No.: US 11,559,271 B2
(45) Date of Patent: Jan. 24, 2023

(54) METHOD AND DATA PROCESSING SYSTEM FOR PROVIDING DECISION-SUPPORTING DATA

(71) Applicant: Siemens Healthcare GmbH, Erlangen (DE)

(72) Inventors: Bernd Hofmann, Erlangen (DE); Sebastian Schmidt, Weisendorf (DE); Kerstin Mueller, San Francisco, CA (US); Yufan Zhao, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 400 days.

(21) Appl. No.: 16/816,747

(22) Filed: Mar. 12, 2020

(65) Prior Publication Data

US 2020/0297299 A1 Sep. 24, 2020

(30) Foreign Application Priority Data

Mar. 19, 2019 (DE) .......................... 102019203714.3

(51) Int. Cl.
*A61B 6/00* (2006.01)
*A61B 6/03* (2006.01)
*G06T 7/00* (2017.01)
*G16H 30/40* (2018.01)
(Continued)

(52) U.S. Cl.
CPC .............. *A61B 6/504* (2013.01); *A61B 6/032* (2013.01); *A61B 6/463* (2013.01); *A61B 6/5217* (2013.01);
(Continued)

(58) Field of Classification Search
CPC ......... A61B 6/504; A61B 6/032; A61B 6/463; A61B 6/5217; G16H 50/20; G16H 30/40;
(Continued)

(56) References Cited

U.S. PATENT DOCUMENTS

| | | | |
|---|---|---|---|
| 2014/0100442 A1* | 4/2014 | Begin | A61B 5/7475 600/414 |
| 2016/0180042 A1* | 6/2016 | Menon | G16H 30/20 705/2 |

(Continued)

FOREIGN PATENT DOCUMENTS

EP     3332710 A1     6/2018

OTHER PUBLICATIONS

Lopez-Linares et al. "Fully automatic detection and segmentation of abdominal aortic thrombus in post-operative CTA images using Deep Convolutional Neural Networks." Med Image Anal. May 2018;46:202-214. doi: 10.1016/j.media.2018.03.010. Epub Mar. 27, 2018. PMID: 29609054. (Year: 2018).*

(Continued)

*Primary Examiner* — Vu Le
*Assistant Examiner* — Julius Chai
(74) *Attorney, Agent, or Firm* — Harness, Dickey & Pierce P.L.C.

(57) ABSTRACT

A method is for providing decision-supporting data. In an embodiment, the method includes receiving photon-counting computed tomography data relating to an examination region; determining a location of a thrombus in the examination region, based on the photon-counting computed tomography data received; generating the decision-supporting data, relating to at least one of the thrombus and a vascular wall in a region of the thrombus, based on the photon-counting computed tomography data received and the location of the thrombus determined; and providing the decision-supporting data generated.

20 Claims, 3 Drawing Sheets

(51) Int. Cl.
*G16H 50/20* (2018.01)
*G06T 11/00* (2006.01)

(52) U.S. Cl.
CPC .......... *G06T 7/0012* (2013.01); *G06T 11/005* (2013.01); *G16H 30/40* (2018.01); *G16H 50/20* (2018.01); *G06T 2207/20081* (2013.01); *G06T 2207/30104* (2013.01); *G06T 2211/404* (2013.01)

(58) Field of Classification Search
CPC ................ G06T 7/0012; G06T 11/005; G06T 2211/404; G06T 2207/20081; G06T 2207/30104
See application file for complete search history.

(56) References Cited

U.S. PATENT DOCUMENTS

| | | | |
|---|---|---|---|
| 2017/0255745 A1* | 9/2017 | Mihalef | G16H 50/50 |
| 2018/0165811 A1 | 6/2018 | Flohr et al. | |
| 2021/0174957 A1* | 6/2021 | Lebedev | A61B 5/7267 |

OTHER PUBLICATIONS

H. A. Hong and U. U. Sheikh, "Automatic detection, segmentation and classification of abdominal aortic aneurysm using deep learning," 2016 IEEE 12th International Colloquium on Signal Processing & Its Applications (CSPA), 2016, pp. 242-246, doi: 10.1109/CSPA.2016.7515839. (Year: 2016).*

R. Gutjahr et al. "Human imaging with photon-counting-based CT at clinical dose levels: Contrast-to-noise ratio and cadaver studies", HHS Public Access, Invest Radiol., 2016, vol. 51, Nr. 7, pp. 421-429, doi:10.1097/RLI.0000000000000251.

A. Pourmorteza et al. "abdominal imaging with contrast-enhanced Photon-counting cT: First Human Experience", Radiology, Technical Developments, 2016, vol. 279, Nr. 1.

D. P. Cormode et al. "Multicolor spectral photon-counting computed tomography: in vivo dual contrast imaging with a high count rate scanner", Scientific Reports, 2017, DOI:10.1038/s41598-017-04659-9.

German Office Action for German Application No. 102019203714.3 dated Mar. 19, 2020.

* cited by examiner

METHOD AND DATA PROCESSING SYSTEM FOR PROVIDING DECISION-SUPPORTING DATA

PRIORITY STATEMENT

The present application hereby claims priority under 35 U.S.C. § 119 to German patent application number DE 102019203714.3 filed Mar. 19, 2019, the entire contents of which are hereby incorporated herein by reference.

FIELD

Embodiments of the invention generally relate to a method and a data processing system for providing decision-supporting data. Embodiments of the invention further generally relate to a computed tomography device, a computer programming product and a computer-readable medium.

BACKGROUND

An essential criterion for a therapeutic decision in a case of ischemic stroke is the time that has passed since the stroke occurred. In a time-window of a plurality of hours after the onset of the stroke and damage to the brain tissue that does not exceed a certain level, a drug for example (e.g. rt-PA) can be administered intravenously to dissolve the vascular occlusion (also referred to below as a clot). In addition, in particular for large vessels, there is also the option to carry out a mechanical thrombectomy, in other words a mechanical re-opening.

Criteria for a therapy are in particular the closure of a large cerebral artery and also the detection of what is known as tissue at risk, i.e. under threat of dying off. At the same time, the volume of the infarct core, i.e. of the irreversibly damaged brain tissue, is not disproportionately large compared with the tissue at risk. The risk can be determined from the representation of the penumbra (reduced blood supply in the tissues without cell death being induced), of the infarct core and of the regularly perfused brain tissue.

Only when a sufficiently large amount of tissue is present that does in fact have a reduced blood supply but has a normal blood supply once the blood flow is restored and at the same time the infarct core is sufficiently small, treatment is indicated either in the form of drug-based lysis therapy or a mechanical thrombectomy.

In every kind of treatment, bleeding into the infarct core presents a significant risk to the patient. This comes about due to the fact that, in areas with reduced perfusion or which are no longer supplied with blood, the vascular wall becomes friable and is no longer able to withstand the high blood pressure that arises to restore perfusion after treatment. The risk of this increases with the time since the onset of the stroke. Furthermore, in the context of a mechanical thrombectomy, the injury to the vascular wall presents a further risk to the patient, as a result of which the blood seeps into the infarct core.

SUMMARY

At least one embodiment of the invention addresses the problem of allowing an improved provision of data for estimating the success and/or risks inherent in a therapeutic decision in the case of ischemic stroke. The problem is improved upon or even solved by the subject matter of each of the independent claims. The dependent claims feature further advantageous aspects of the invention.

At least one embodiment of the invention relates to a method for providing decision-supporting data, which includes the following steps:
receiving photon-counting computed tomography data relating to an examination region,
determining a location of a thrombus in the examination region, based on the photon-counting computed tomography data,
generating the decision-supporting data that relates to the thrombus and/or to a vascular wall in the region of the thrombus, based on the photon-counting computed tomography data and the location of the thrombus, and
providing the decision-supporting data.

Based on photon-counting computed tomography data, anatomical structures can be displayed with a very high spatial resolution, in an energy-resolved manner and with a negligible amount of electronic noise. Various relevant information can be extracted therefrom with a high degree of accuracy and provided to support a decision related to therapy for a stroke. One embodiment makes provision for
a computed tomography angiographic image to be generated based on the photon-counting computed tomography data,
the location of the thrombus in the examination region to be determined based on the computed tomography angiographic image, and
for the decision-supporting data that relates to the thrombus and/or to the vascular wall in the region of the thrombus to be generated based on the computed tomography angiographic image.

At least one embodiment of the invention further relates to a data processing system for providing decision-supporting data, including:
a receiving unit for receiving photon-counting computed tomography data relating to an examination region,
a determination unit for determining a location of a thrombus in the examination region, based on the photon-counting computed tomography data,
a generating unit for generating the decision-supporting data, which relates to the thrombus and/or a vascular wall in the region of the thrombus, based on the photon-counting computed tomography data and on the location of the thrombus, and
a preparation unit for providing the decision-supporting data.

At least one embodiment of the invention further relates to a computed tomography device, comprising a data processing system for providing decision-supporting data according to one of the features that have been disclosed.

At least one embodiment of the embodiment makes provision for the computed tomography device to have a photon-counting detector and/or to be embodied for the acquisition of photon-counting computed tomography data.

At least one embodiment of the invention further relates to a computer program product with a computer program which can be loaded directly into a memory unit of a data processing system, with program segments to carry out all the steps in a method according to one of the features that have been disclosed when the program segments are run by the data processing system.

At least one embodiment of the invention further relates to a computer-readable storage medium, on which are stored program segments that can be read and executed by a data processing system in order to carry out all the steps of a method according to one of the features that have been disclosed when the program segments are run by the data processing system.

At least one embodiment of the invention further relates to a data processing system for providing decision-supporting data, comprising:

a receiving unit to receive photon-counting computed tomography data relating to an examination region;

a determination unit to determine a location of a thrombus in the examination region, based on the photon-counting computed tomography data received;

a generating unit to generate the decision-supporting data relating to at least one of the thrombus and a vascular wall in a region of the thrombus, based on the photon-counting computed tomography data received and on the location of the thrombus determined; and a preparation unit to prove the decision-supporting data generated.

At least one embodiment of the invention further relates to a non-transitory computer program product storing a computer program, directly loadable into a memory unit of a data processing system, including program segments to carry out the method of an embodiment when the program segments are run by the data processing system.

At least one embodiment of the invention further relates to a non-transitory computer-readable storage medium, storing program segments readable and executable by a data processing system, to carry out the method of an embodiment upon the program segments being run by the data processing system.

BRIEF DESCRIPTION OF THE DRAWINGS

The invention is described in further detail hereinafter by way of example embodiments with reference to the attached figures. The view shown in the figures is schematic, highly simplified and not necessarily true to scale.

The figures show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising,"

"includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for providing decision-supporting data, which includes the following steps:

receiving photon-counting computed tomography data relating to an examination region, determining a location of a thrombus in the examination region, based on the photon-counting computed tomography data, generating the decision-supporting data that relates to the thrombus and/or to a vascular wall in the region of the thrombus, based on the photon-counting computed tomography data and the location of the thrombus, and providing the decision-supporting data.

In particular, the method for providing decision-supporting data can be a computer-implemented method and/or can be performed in a fully automatic manner. Based on the decision-supporting data provided, a therapeutic decision relating to ischemic stroke, for example, can be generated in a fully automatic manner. The examination region can be in particular a patient's head or a sub-region of a patient's head.

The location of the thrombus in the examination region can be determined by, for example, identifying potential vascular damage, in particular in the form of a vascular constriction, a vascular cut-off and/or a vascular occlusion, based on the photon-counting computed tomography data and by determining the location of the potential vascular damage. Due to the high spatial resolution of the photon-counting computed tomography data compared with conventional computed tomography data that has been recorded by indirect conversion, even very small vascular injuries can be identified and located.

Photon-counting computed tomography data is understood to mean computed tomography data, which has as its basis spectrally resolved projection data that has been recorded using photon-counting detectors. Photon-counting computed tomography data can be used, for example, in the form of mixed images, virtual non-contrast (VNC) images, iodine maps and/or single-energy images.

Based on photon-counting computed tomography data, anatomical structures can be displayed with a very high spatial resolution, in an energy-resolved manner and with a negligible amount of electronic noise. Various relevant information can be extracted therefrom with a high degree of accuracy and provided to support a decision related to therapy for a stroke. One embodiment makes provision for a computed tomography angiographic image to be generated based on the photon-counting computed tomography data, the location of the thrombus in the examination region to be determined based on the computed tomography angiographic image, and for the decision-supporting data that relates to the thrombus and/or to the vascular wall in the region of the thrombus to be generated based on the computed tomography angiographic image.

In particular, hypodense areas in the examination region can first be identified based on the photon-counting computed tomography data, for example based on a non-contrasted computed tomography image. The hypodense areas can then be displayed in the form of a computed tomography angiographic image.

The decision-supporting data can be provided, for example, in the form of graphic elements and/or in the form of color-coded quantitative information. In particular, in the computed tomography angiographic image for each voxel in the region of a vessel, a probability of a potential thrombus that contains this voxel can be displayed by way of color-coding using an appropriate color for the voxel.

Alternatively, and/or additionally, the decision-supporting data can be displayed as a function of a user input in a graphic user interface that encompasses the computed tomography angiographic image. The user input can be in particular the selection of a voxel by the user, for example via a movement and/or of a computer input device, in the form of a touch-sensitive screen and/or a mouse, for example. The decision-supporting data can then include in particular quantitative information which relates to the selected voxel.

One embodiment makes provision for marking information that marks the thrombus in the computed tomography angiographic image to be generated based on the photon-counting computed tomography data and on the location of the thrombus, and for the computed tomography angiographic image, the marking information that marks the thrombus in the computed tomography angiographic image, and the decision-supporting data to be provided for simultaneous display on a screen.

In particular, the marking information in the computed tomography angiographic image can be displayed superimposing an anatomical structure, for example a vascular structure.

One embodiment makes provision for the location of the thrombus to be determined by the calculation thereof by applying a trained machine learning algorithm to the photon-counting computed tomography data and/or to the computed tomography angiographic image, using a computation unit, for example.

In the context of the present application, a machine learning algorithm is understood in particular to mean an algorithm that is embodied for machine learning. The machine learning algorithm can be embodied for monitored learning and/or for unmonitored learning, for example. The machine learning algorithm can be embodied, for example, for deep learning and/or for reinforcement learning and/or for marginal space learning.

The machine learning algorithm can be based, for example, on decision trees, a random forest, a logistic regression, a support vector machine, an artificial neural network, in particular a convolutional neural network and/or a recurrent neural network, a kernel method, Bayes classifiers or suchlike or on combinations thereof.

Calculations, in particular when training a machine learning algorithm, can be carried out via a processor system, for example. The processor system can comprise one or a plurality of processors, for example, in particular graphic processors.

The trained machine learning algorithm can be in particular a neural network that has been trained by way of a deep learning method. In particular, the trained machine learning algorithm can be embodied to identify potential vascular damage, in particular in the form of a vascular constriction, a vascular cut-off, and/or a vascular occlusion based on the photon-counting computed tomography data, and to determine the location thereof.

One embodiment makes provision for the decision-supporting data to relate to at least one property of the thrombus, which is selected from a group of properties that consists of a length, a diameter, a volume, a perviousness and a composition. The diameter and/or the volume of the thrombus can be calculated based on the segmentation of the thrombus, for example.

The decision-supporting data, in particular properties of the thrombus and/or properties of the vascular wall in the region of the thrombus, can be calculated in particular by applying a trained machine learning algorithm for calculating decision-supporting data to the photon-counting computed tomography data and/or to the computed tomography angiographic image.

One embodiment makes provision for a segmentation of the thrombus to be calculated based on the photon-counting computed tomography data, and/or for a vascular center line that extends through the thrombus to be calculated based on the photon-counting computed tomography data. A length of the thrombus can be calculated, in particular based on the vascular center line and the segmentation of the thrombus.

The length of the thrombus can be calculated, for example, by calculating the length of a section of the vascular center line that is located inside the segmentation of the thrombus, in particular can be calculated automatically. In particular, the segmentation of the thrombus, the vascular center line and the length of the thrombus can be calculated in a fully automatic manner. In particular, a segmentation of the vascular wall in the region of the thrombus can be calculated. In particular, the vascular center line can be calculated based on the segmentation of the vascular wall in the region of the thrombus.

The length of the thrombus can be a decision-making criterion for stroke therapy. In particular, stroke therapy is to be considered as more likely to succeed if the length of the thrombus falls below a given threshold value. If the length of the thrombus is relatively short, a recanalization of the vessel in the region of the thrombus by way of intravenous thrombolytic therapy has better prospects of success.

One embodiment makes provision for a flow of contrast medium that penetrates the thrombus to be calculated based on the photon-counting computed tomography data. The perviousness of the thrombus can be calculated in particular based on the flow of contrast medium.

In particular, the photon-counting computed tomography data can include dynamic information and/or perfusion data. In particular, a multi-phase computed tomography angiographic image that includes the dynamic information can be generated based on the photon-counting computed tomography data. The flow of contrast medium in particular can be calculated based on the dynamic information and/or the perfusion data.

In addition, the thrombus perviousness can be calculated based on the photon-counting computed tomography data in the form of a virtual non-contrast image, it being possible to determine how much blood or contrast medium penetrates the thrombus. The perviousness of the thrombus can be provided in particular in the form of at least one of two defined parameters, the void fraction and the thrombus attenuation increase (TAI).

The perviousness of the thrombus correlates with a better revascularization rate, a smaller infarct core and a better functional therapeutic success of intravenous thrombolytic therapy, for example with rt-PA.

If the perviousness of the thrombus exceeds a given threshold value such that the cells in the vascular wall in the region of the thrombus can be supplied with blood, there is a greater probability that the vascular wall is essentially intact and can withstand the restitution of normal blood flow. Due to the high spatial resolution and the spectral resolution, the use of photon-counting computed tomography data allows the calculation in particular of relatively low values for the perviousness of the thrombus, yet which are sufficient to guarantee the integrity of the vascular wall. The calculation of the perviousness of the thrombus makes it possible in particular to estimate whether lysis therapy can be carried out with a good chance of success even outside a given time window, for example after four and a half hours have elapsed since the onset of the stroke.

The supply of blood to the tissue at risk and/or to the vascular wall in the region of the thrombus can ensue, for example, via bypass vessels (known as bridge vessels or collaterals) that bridge the thrombus. As a result, the ability of the tissue with decreased perfusion to survive and/or the integrity of the vascular wall can be guaranteed in a certain framework.

The extent of the blood flow through the bypass vessels can be determined, for example based on perfusion data, in particular cerebral perfusion data, which is contained in the photon-counting computed tomography data. In particular, a blood flow through bypass vessels that bridge the thrombus can be calculated by applying a trained machine learning algorithm for calculating the bypass blood flow to the photon-counting computed tomography data and/or to the computed tomography angiographic image.

One embodiment makes provision for the decision-supporting data to relate to, in particular to include, part of a component in the composition of the thrombus, said component being selected from the group of components that consist of red blood corpuscles, an accumulation of fibrin platelets and calcium.

The composition of the thrombus can be determined based on the spectral information in the photon-counting computed tomography data. In particular, for each of the components in the group of components, a percentage of the volume and/or of the mass of the thrombus can be calculated. From the composition of the thrombus it can be estimated, for example, whether a mechanical thrombectomy and/or lysis therapy of the thrombus can be successful.

Depending on its composition, the thrombus can have a rather soft or a rather hard consistency. For example, based on the composition of the thrombus, a clot-retriever can be configured for the mechanical thrombectomy and/or one of a plurality of differently configured clot-retrievers can be selected for the mechanical thrombectomy. In particular, the geometry of a clot-retriever for the mechanical thrombectomy can be optimized based on the composition of the thrombus.

One embodiment makes provision for the decision-supporting data to include in particular a perviousness of the vascular wall in the region of the thrombus.

Based on the perviousness of the vascular wall in the region of the thrombus, a probability of a rupture of the vascular wall during the restitution of normal blood flow can be determined. Furthermore, the perviousness of the vascular wall is a parameter for the integrity of the blood-brain barrier. The perviousness of the vascular wall can be provided for example in the form of a transendothelial transfer constant (kPS) and/or in the form of a surface area product (PS), for example using the unit [mL/100 g/min].

The decision-supporting data can include, for example, an indicator that indicates whether the vascular wall is friable or is inclined to be friable. The indicator that indicates whether the vascular wall is friable or is inclined to be friable can be calculated in particular by applying a trained machine learning algorithm for calculating the friability of the vascular wall to the photon-counting computed tomography data and/or to the computed tomography angiographic image.

Based on such an indicator, it is possible, for example, to state whether there is an increased risk of bleeding or whether the integrity of the vascular wall is still maintained. The former can be, for example, a contraindication for intravenous lysis therapy after the expiry of 4.5 hours since the onset of the stroke. Therefore, the risk of bleeding into the infarct core due to a friable vascular wall can be minimized after therapy has been administered.

One embodiment makes provision for a flow of contrast medium that penetrates the vascular wall in the region of the thrombus to be calculated based on the photon-counting computed tomography data. The perviousness of the vascular wall in the region of the thrombus can be calculated in particular based on the flow of contrast medium.

The perviousness of the vascular wall can be calculated, for example, based on dynamic information and/or perfusion data that is contained in the photon-counting computed tomography data and/or in the computed tomography angiographic image. Here the seepage of intravascular contrast medium into the extravascular (interstitial) space can be measured.

One embodiment makes provision for an accumulation of contrast medium that has penetrated the vascular wall in the region of the thrombus to be detected based on the photon-counting computed tomography data and/or for marking information that marks the accumulation of contrast medium that has penetrated the vascular wall in the region of the thrombus to be generated based on the photon-counting computed tomography data.

The decision-supporting data can include in particular the marking information that marks the accumulation of contrast medium that has penetrated the vascular wall in the region of the thrombus.

Due to the high spatial resolution of the photon-counting computed tomography data and the possibility of generating a virtual non-contrast image, even a very slight amount of, for example, an iodine-containing contrast medium which seeps out of the blood vessel into surrounding tissue and in the process penetrates the vascular wall in the region of the thrombus can be determined in a sensitive manner. In particular, voxels that indicate iodine-containing contrast medium in the vicinity of a blood vessel inside the identified hypodense area can be marked in color as a rupture-risk area.

The decision-supporting data, in particular each aforementioned property of the thrombus and/or of the vascular wall, can be calculated in a fully automatic manner and provided in a fully automatic manner to support the therapeutic decision-making. In this way, a better estimate by the medical staff providing treatment of a success and/or of risks inherent in a therapeutic decision is possible in the case of ischemic stroke. Furthermore, on this basis, therapeutic decisions can be made in a standardized and reproducible manner.

At least one embodiment of the invention further relates to a data processing system for providing decision-supporting data, including:

a receiving unit for receiving photon-counting computed tomography data relating to an examination region, a determination unit for determining a location of a thrombus in the examination region, based on the photon-counting computed tomography data, a generating unit for generating the decision-supporting data, which relates to the thrombus and/or a vascular wall in the region of the thrombus, based on the photon-counting computed tomography data and on the location of the thrombus, and a preparation unit for providing the decision-supporting data.

One embodiment makes provision for the data processing system to be embodied for executing a method for providing decision-supporting data according to one of the features that have been disclosed.

At least one embodiment of the invention further relates to a computed tomography device, comprising a data processing system for providing decision-supporting data according to one of the features that have been disclosed.

At least one embodiment of the embodiment makes provision for the computed tomography device to have a photon-counting detector and/or to be embodied for the acquisition of photon-counting computed tomography data.

At least one embodiment of the invention further relates to a computer program product with a computer program which can be loaded directly into a memory unit of a data processing system, with program segments to carry out all the steps in a method according to one of the features that have been disclosed when the program segments are run by the data processing system.

The computer program product can be a computer program, for example, or include at least one additional component alongside the computer program. The at least one additional component of the computer program product can be embodied as hardware and/or as software.

The computer program product can be a storage medium, for example, on which at least one part of the computer program product is stored, and/or have a key for authenticating a user of the computer program product, in particular in the form of a dongle. The computer program product and/or the computer program can comprise a cloud-application program, for example, which is embodied to distribute program segments of the computer program to various processing units, in particular various computers in a Cloud Computing System, each of the processing units being embodied to run one or a plurality of program segments of the computer program.

At least one embodiment of the invention further relates to a computer-readable storage medium, on which are stored program segments that can be read and executed by a data processing system in order to carry out all the steps of a method according to one of the features that have been disclosed when the program segments are run by the data processing system.

On the computer-readable storage medium it is possible, for example, for the computer program product according to one of the embodiments that are disclosed in the present application and/or for the computer program according to one of the embodiments that are disclosed in the present application to be stored. The computer-readable medium can be, for example, a memory stick, a hard disk or another data-carrier that can be in particular detachably connected to the data processing system or fixedly incorporated into the data processing system. The computer-readable medium can form, for example, a region of the storage system of the data processing system.

The data processing system can have, for example, one or a plurality of components in the form of hardware and/or one or a plurality of components in the form of software. The data processing system can, for example, be at least partly formed of a Cloud Computing System. The data processing system can for example, be and/or comprise a Cloud Computing System, a computer network, a computer, a tablet, a smartphone or suchlike or a combination thereof.

The hardware can, for example, interact with software and/or be configurable using software. The software can be, for example, executed using the hardware. The hardware can be, for example, a storage system, an FPGA (field-programmable gate array) system, an ASIC (application-specific integrated circuit) system, a microcontroller system, a processor system and combinations thereof. The processor system can comprise, for example, a microprocessor and/or a plurality of interacting microprocessors.

The steps in the method can be carried out, for example, in a processor, in particular in the form of calculations.

A data transfer between components of the data processing systems can ensue, for example, using in each case an appropriate data transfer interface. The data transfer interface for the data transfer to and/or from a component of the data processing system can be at least partly implemented in the form of software and/or at least partly in the form of hardware. The data transfer interface can be embodied, for example, for the storage of data in and/or for importing data from a region of the storage system, wherein one or a plurality of components of the data processing system can access this region of the storage system.

Data, in particular the photon-counting computed tomography data, can be received, for example, by a signal that carries the data being received and/or by the data being imported, in particular imported from a computer-readable storage medium. Data, in particular the decision-supporting data, can be provided, for example by a signal that carries the data being transmitted and/or the data being entered into a computer-readable storage medium and/or by the data being displayed on a screen.

In the context of the invention, features that are described in relation to different embodiments of the invention and/or to different categories of claim (method, use, apparatus, system, array etc.) can be combined to form further embodiments of the invention. For example, a claim that relates to an apparatus can also be further developed with features that have been described or claimed in conjunction with a method and vice versa. Here, functional features of a method can be carried out by appropriately embodied concrete components. In addition to the embodiments of the invention that have been described explicitly in this application, diverse further embodiments of the invention at which a person skilled in the art will arrive without going beyond the scope of the invention as set out in the claims are conceivable.

The expression "based on" can be understood in the context of the present application in particular in the sense of the expression "using". In particular, a wording according to which a first feature is created (alternatively: acquired, determined etc.) based on a second feature does not preclude the first feature from being able to be created (alternatively: acquired, determined etc.) based on a third feature.

Figure 1:
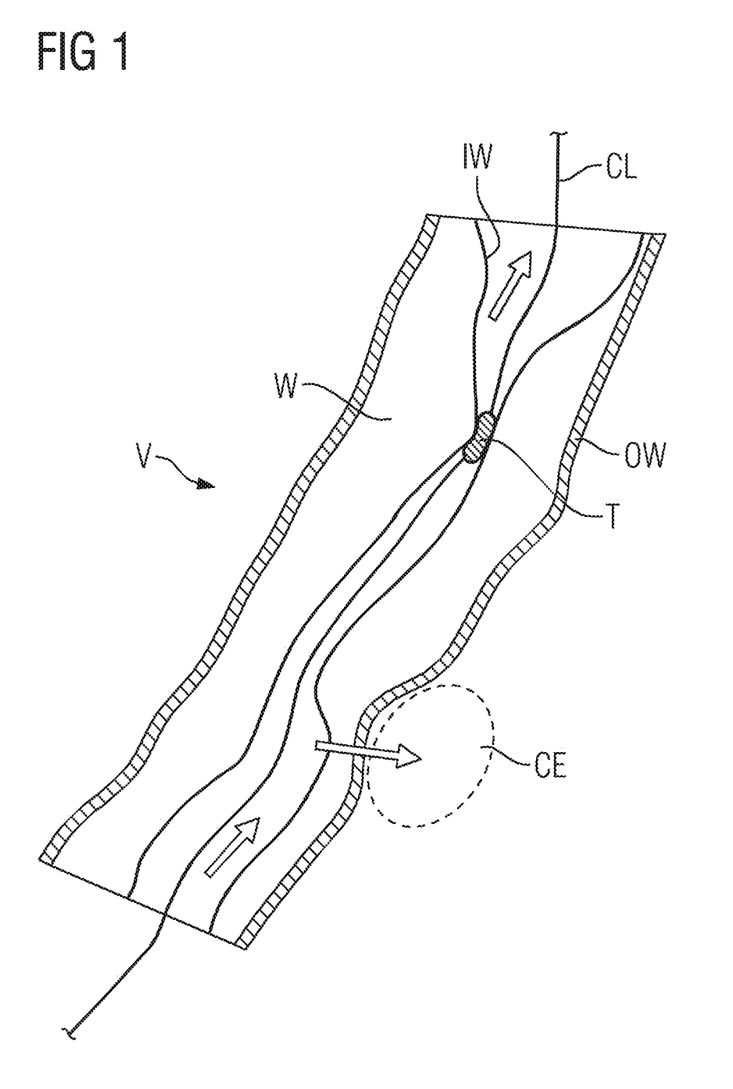
FIG. 1: a vascular section in the region of a thrombus.

FIG. 1 shows a vascular section V in the region of the thrombus T. The vascular wall W of the vascular section V is delimited by an outer wall OW and an inner wall IW. The vascular center line CL extends through the lumen of the blood vessel that is delimited by the inner wall IW. The arrows show the blood flow in the vascular section V. Part of the blood flow penetrates through the vascular wall W in the region of the thrombus T and forms an accumulation CE of contrast medium, which has penetrated the vascular wall W in the region of the thrombus T.

Figure 2:
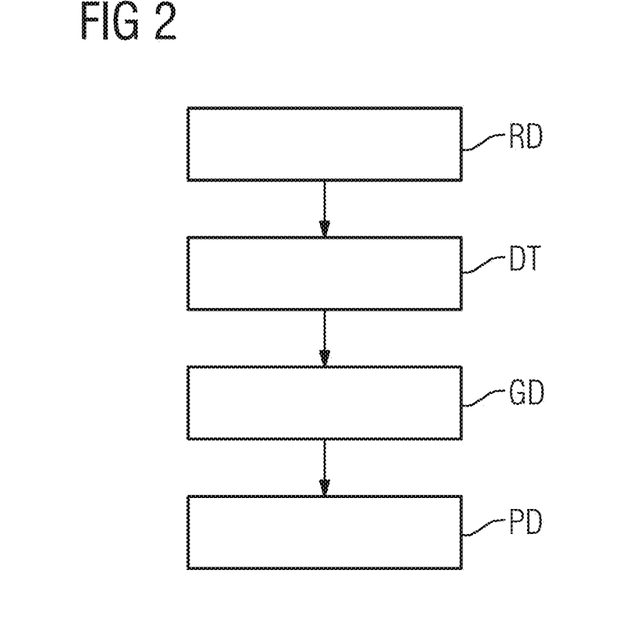
FIG. 2: a flow chart for a method for providing decision-supporting data.

FIG. 2 shows a method for providing decision-supporting data, which includes the following steps:
receiving RD photon-counting computed tomography data relating to an examination region,
determining DT a location of a thrombus T in the examination region based on the spectrally resolved photon-counting computed tomography data,
generating GD the decision-supporting data, which relates to the thrombus T and/or a vascular wall W in the region of the thrombus T based on the photon-counting computed tomography data and the location of the thrombus T, and
providing PD the decision-supporting data.

Figure 3:
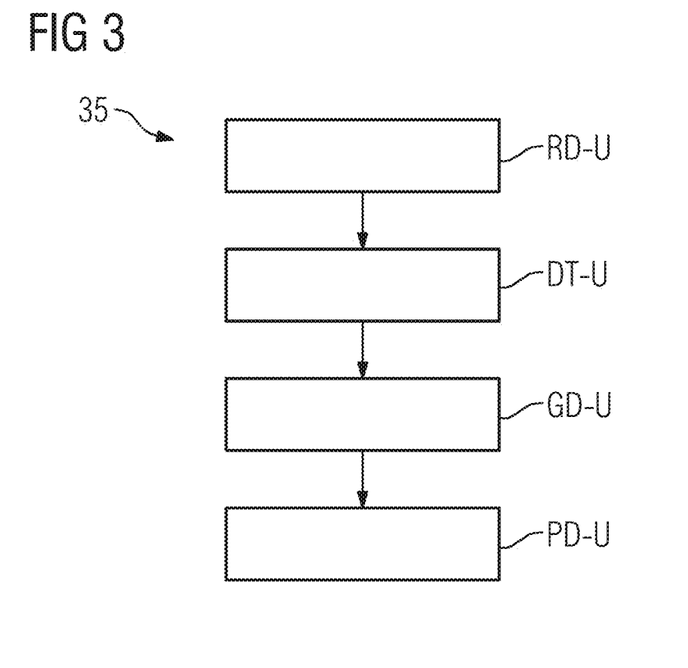
FIG. 3: a data processing system for providing decision-supporting data.

FIG. 3 shows a data processing system 35 for providing decision-supporting data, including:
a receiving unit RD-U for receiving RD photon-counting computed tomography data relating to an examination region,
a determination unit DT-U for determining DT a location of a thrombus T in the examination region based on the spectrally resolved photon-counting computed tomography data,
a generating unit GD-U for generating GD the decision-supporting data that relates to the thrombus T and/or a vascular wall in the region of the thrombus T based on the photon-counting computed tomography data and on the location of the thrombus T, and
a preparation unit PD-U for providing PD the decision-supporting data.

Figure 4:
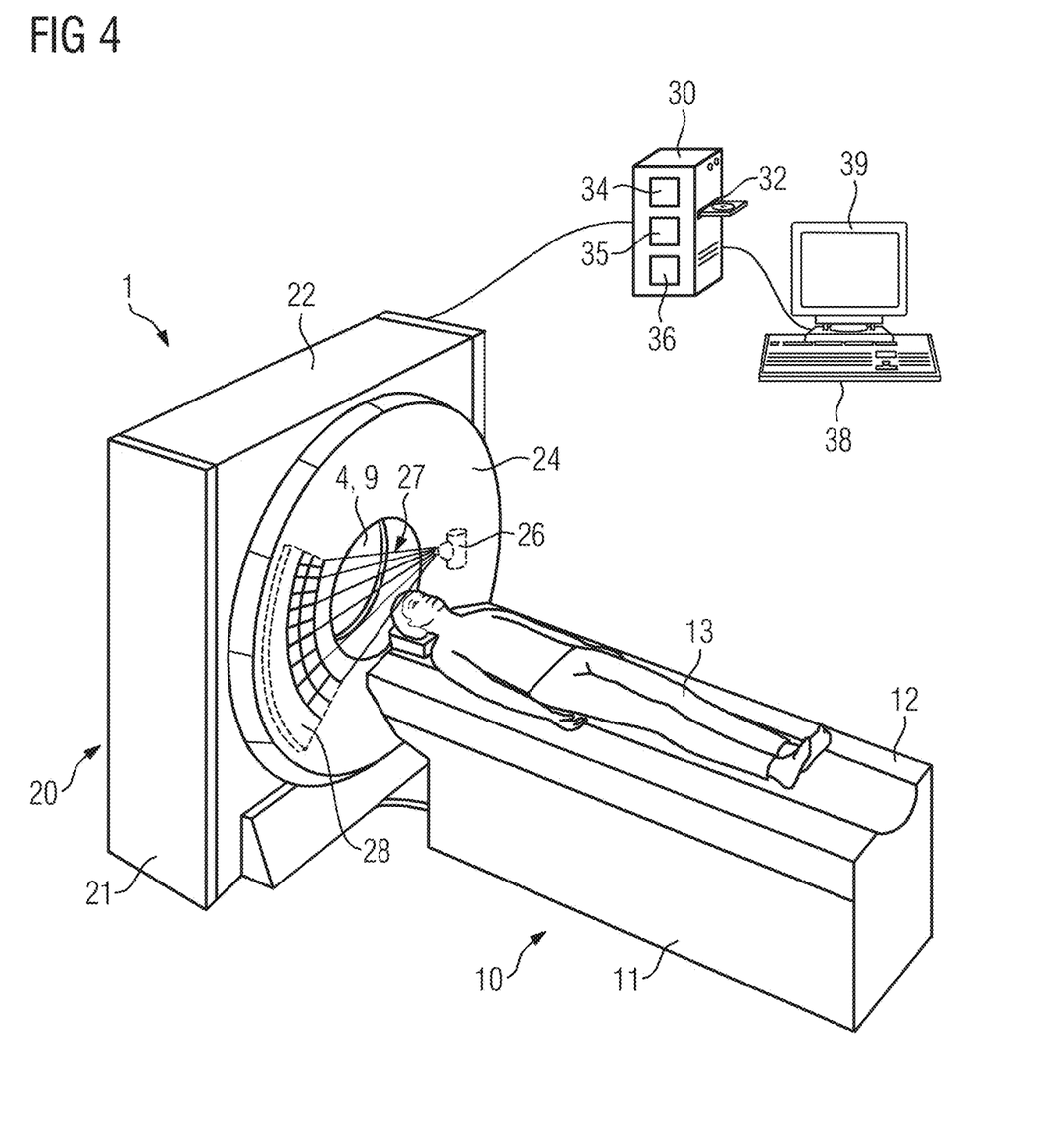
FIG. 4: a computed tomography device.

FIG. 4 shows a computed tomography device 1, comprising the gantry 20, the tunnel-shaped aperture 9, the patient-positioning device 10 and the control device 30. The gantry 20 comprises the stationary supporting frame 21, the tilting frame 22 and the rotor 24.

The tilting frame 22 is tiltably arranged around a tilt axis relative to the stationary supporting frame 21 via a tilt positioning device on the stationary supporting frame 21. The rotor 24 is rotatably arranged around a rotation axis relative to the tilting frame 22 via a rotational positioning device on the tilting frame 22.

The patient 13 can be inserted in the tunnel-shaped aperture 9. In the tunnel-shaped aperture 9 is the acquisition region 4. In the acquisition region 4, a region of the patient 13 that is to be imaged can be positioned, such that the radiation 27 from the x-ray source 26 can reach the region to be imaged and after interaction with the region to be imaged can reach the x-ray detector 28.

The patient positioning device 10 comprises the positioning base 11 and the positioning plate 12 for positioning the patient 13. The positioning plate 12 is moveably arranged on the positioning base 11 relative to the positioning base 11 such that, in a longitudinal direction of the positioning plate 12, the positioning plate 12 is insertable into the acquisition region 4.

The computed tomography device is embodied for the acquisition of acquisition data, based on electromagnetic radiation 27. The computed tomography device 1 comprises an acquisition unit. The acquisition unit is a projection data acquisition unit comprising the radiation source 26, for example an x-ray source, and the photon-counting detector 28.

The radiation source 26 is arranged on the rotor 24 and is embodied for the emission of radiation 27, of x-rays, for example, with radiation quanta 27. The detector 28 is arranged on the rotor 24 and is embodied for the detection of the radiation quanta 27 by way of direct conversion. The radiation quanta 27 can go from the radiation source 26 to the region of the patient 13 that is to be imaged and, after interaction with the region to be imaged, can reach the x-ray detector 28. In this way, acquisition data for the region to be imaged can be acquired via the acquisition unit in the form of spectrally resolved projection data.

The control device 30 is embodied for receiving the acquisition data acquired by the acquisition unit. The control device 30 is embodied for controlling the computed tomography device 1. The control device 30 comprises the data processing system 35, the computer-readable medium 32 and the processor system 36. The control device 30, in particular the data processing system 35, takes the form of a computer.

The control device 30 comprises the image reconstruction device 34. By way of the image reconstruction device 34, photon-counting computed tomography data can be generated based on the spectrally resolved projection data.

The computed tomography device 1 comprises an input device 38 and an output device 39, each of which is connected to the control device 30. The input device 38 is embodied for inputting control information, such as image reconstruction parameters, examination parameters or suchlike. The output device 39 is embodied in particular for outputting control information, images and/or acoustic signals.

The output device 9 can comprise a screen, for example, to display a graphic user interface, which includes the computed tomography angiographic image, the marking information that marks the thrombus T in the computed tomography angiographic image, and the decision-supporting data.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing decision-supporting data, the method comprising:
   receiving photon-counting computed tomography data relating to an examination region;
   determining a location of a thrombus in the examination region, based on the photon-counting computed tomography data;
   generating decision-supporting data relating to a composition of the thrombus, determined from the photon-counting computed tomography data and the location of the thrombus, the decision-supporting data relating to a portion of red blood cell corpuscles in the composition of the thrombus, a portion of fibrin platelets in the composition of the thrombus, and a portion of calcium in the composition of the thrombus; and
   providing the decision-supporting data.

2. The computer-implemented method of claim 1, further comprising:
   generating a computed tomography angiographic image based on the photon-counting computed tomography data; wherein
   the location of the thrombus in the examination region is determined based on the computed tomography angiographic image, and
   the decision-supporting data is generated based on the computed tomography angiographic image.

3. The computer-implemented method of claim 2, further comprising:
   generating marking information, marking the thrombus in the computed tomography angiographic image, based on the photon-counting computed tomography data and the location of the thrombus; and
   providing the computed tomography angiographic image, the marking information, and the decision-supporting data for simultaneous display on a screen.

4. The computer-implemented method of claim 2, wherein the determining of the location of the thrombus comprises:
   calculating the location of the thrombus by applying a trained machine learning algorithm to at least one of the photon-counting computed tomography data or the computed tomography angiographic image.

5. The computer-implemented method of claim 1, wherein the decision-supporting data also relates to at least one property of the thrombus, selected from at least one of a length, a diameter, a volume, or a perviousness.

6. The computer-implemented method of claim 5, further comprising:
   calculating a segmentation of the thrombus based on the photon-counting computed tomography data;
   calculating a vascular center line extending through the thrombus based on the photon-counting computed tomography data; and
   calculating a length of the thrombus based on the vascular center line and the segmentation of the thrombus.

7. The computer-implemented method of claim 5, further comprising:
   calculating a flow of contrast medium penetrating the thrombus based on the photon-counting computed tomography data; and
   calculating the perviousness of the thrombus based on the flow of contrast medium.

8. The computer-implemented method of claim 1, wherein the decision-supporting data further relates to a perviousness of a vascular wall in a region of the thrombus.

9. The computer-implemented method of claim 8, further comprising:
   calculating a flow of contrast medium penetrating the vascular wall in the region of the thrombus based on the photon-counting computed tomography data; and
   calculating the perviousness of the vascular wall in the region of the thrombus based on the flow of contrast medium.

10. The computer-implemented method of claim 1, further comprising:
    detecting an accumulation of contrast medium that has penetrated a vascular wall in a region of the thrombus based on the photon-counting computed tomography data;
    generating marking information marking the accumulation of contrast medium; and wherein
    the decision-supporting data includes the marking information marking the accumulation of contrast medium.

11. The computer-implemented method of claim 3, wherein the determining of the location of the thrombus comprises:
    calculating the location of the thrombus by applying a trained machine learning algorithm to at least one of the photon-counting computed tomography data or the computed tomography angiographic image.

12. The computer-implemented method of claim 1, wherein the determining of the location of the thrombus comprises:
    calculating the location of the thrombus by applying a trained machine learning algorithm to the photon-counting computed tomography data.

13. The computer-implemented method of claim 2, wherein the decision-supporting data further relates to at least one property of the thrombus, the at least one property selected from a length, a diameter, a volume, or a perviousness.

14. The computer-implemented method of claim 6, further comprising:
- calculating a flow of contrast medium penetrating the thrombus based on the photon-counting computed tomography data; and
- calculating the perviousness of the thrombus based on the flow of contrast.

15. The computer-implemented method of claim 1, wherein the method is non-invasive.

16. A data processing system for providing decision-supporting data, the data processing system comprising:
- at least one processor; and
- a memory configured to store instructions that, when executed by the at least one processor, cause the data processing system to:
  - receive photon-counting computed tomography data relating to a n examination region,
  - determine a location of a thrombus in the examination region, based on the photon-counting computed tomography data,
  - generate decision-supporting data relating to a composition of the thrombus, determined from the photon-counting computed tomography data and the location of the thrombus, the decision-supporting data relating to a portion of red blood cell corpuscles in the composition of the thrombus, a portion of fibrin platelets in the composition of the thrombus, and a portion of calcium in the composition of the thrombus, and
  - provide the decision-supporting data.

17. A computed tomography device, comprising the data processing system of claim 16.

18. A non-transitory computer program product storing a computer program, loadable into a memory of a data processing system, the computer program including program segments to carry out the method of claim 1 when the program segments are executed by the data processing system.

19. A non-transitory computer-readable storage medium, storing program segments that, when executed by a data processing system, cause the data processing system to carry out the method of claim 1.

20. A non-transitory computer-readable storage medium, storing program segments that, when executed by a data processing system, cause the data processing system to carry out the method of claim 2.

* * * * *